United States Patent
Crooks et al.

(10) Patent No.: US 6,417,359 B1
(45) Date of Patent: Jul. 9, 2002

(54) PHARMACEUTICAL COMPOSITIONS AND METHODS FOR USE

(75) Inventors: Peter Anthony Crooks, Lexington, KY (US); Haeil Park, Kangwon-do (KR); Balwinder Singh Bhatti, Winston-Salem, NC (US); William Scott Caldwell, Winston-Salem, NC (US); Gary Maurice Dull, Lewisville, NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 09/560,421

(22) Filed: Apr. 27, 2000

Related U.S. Application Data

(62) Division of application No. 09/053,937, filed on Apr. 2, 1998, now Pat. No. 6,057,446.

(51) Int. Cl.[7] .................. C07D 401/04; C07D 403/04; C07P 239/22
(52) U.S. Cl. ................ 544/298; 544/299; 544/309; 544/317; 544/323; 544/326; 544/330; 544/332
(58) Field of Search ................ 544/330, 332, 544/97, 278, 299, 309, 317, 323, 326

(56) References Cited

U.S. PATENT DOCUMENTS

| | | | |
|---|---|---|---|
| 5,110,933 A | 5/1992 | Berlin et al. | 546/114 |
| 5,219,849 A | 6/1993 | Lotti et al. | 514/214.03 |
| 5,346,906 A | 9/1994 | Baker et al. | 514/305 |
| 5,510,355 A | 4/1996 | Bencherif et al. | 514/305 |
| 5,583,140 A | 12/1996 | Bencherif et al. | 514/299 |
| 5,684,159 A | 11/1997 | O'Brien et al. | 549/452 |

FOREIGN PATENT DOCUMENTS

| EP | WO 95/03306 | 2/1995 |
|---|---|---|

OTHER PUBLICATIONS

Becker et al., *Synthesis*, vol. 11, pp. 1080–1082, (Nov. 1992).
Fernanded et al., *J. Hetercycl. Chem.*, vol. 26, pp. 349–353.
Lau et al., *J. Amer. Chem. Soc.*, 117, pp. 11421–11425 (1995).
Speckamp et al., *Hetercycles*, 2, pp. 293–296 (1974).
Holladay et al., *J. Med. Chem.*, vol. 40, No. 26, pp. 4169–4194.
Henkel et al., *J. Org. Chem.*, 46, pp. 3483–3486 (1981).

*Primary Examiner*—Alan L. Rotman
(74) *Attorney, Agent, or Firm*—Womble Carlyle Sandridge & Rice, PLLC

(57) ABSTRACT

A compound having the formula:

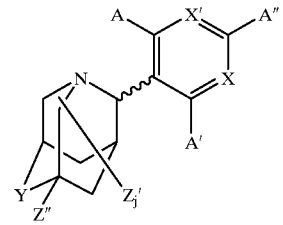

wherein X' is nitrogen or carbon bonded to a substituent species characterized as having a sigma m value greater than 0, less than 0 or 0; X is nitrogen or carbon bonded to a substituent species characterized as having a sigma m value greater than 0, less than 0, but not equal to 0; A, A' and A" are individually substituent species characterized as having a sigma m value greater than 0, less than 0 or 0; Z' is a substituent other than hydrogen; j is an integer from 0 to 5; and the wavy line in the structure indicates that the compound can exist in the form of an enantiomer or a diasteromer; Z" is hydrogen or a substituent other than hydrogen; Y is C=O, C(OH)R' or C—A, where R' is hydrogen or lower alkyl.

5 Claims, No Drawings

PHARMACEUTICAL COMPOSITIONS AND METHODS FOR USE

This application is a divisional of application Ser. No. 09/053,937, filed Apr. 2, 1998 now of U.S. Pat. No. 6,057,446, which issued on May 2, 2000, the disclosure of which is incorporated herein by reference.

BACKGROUND OF THE INVENTION

The present invention relates to pharmaceutical compositions, and particularly pharmaceutical compositions incorporating compounds that are capable of affecting nicotinic cholinergic receptors. More particularly, the present invention relates to compounds capable of acting to inhibit function of certain nicotinic cholinergic receptors, and hence acting as antagonists at certain specific nicotinic receptor subtypes. The present invention also relates to methods for treating a wide variety of conditions and disorders, including conditions and disorders associated with dysfunction of the central and autonomic nervous systems.

Nicotine has been proposed to have a number of pharmacological effects. See, for example, Pullan et al. *N. Engl. J. Med.* 330:811–815 (1994). Certain of those effects may be related to effects upon neurotransmitter release. See for example, Sjak-shie et al., *Brain Res.* 624:295 (1993), where neuroprotective effects of nicotine are proposed. Release of acetylcholine and dopamine by neurons upon administration of nicotine has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons upon administration of nicotine has been reported by Hall et al., *Biochem. Pharmacol.* 21:1829 (1972). Release of serotonin by neurons upon administration of nicotine has been reported by Hery et al., *Arch. Int. Pharmacodyn. Ther.* 296:91 (1977). Release of glutamate by neurons upon administration of nicotine has been reported by Toth et al., *Neurochem Res.* 17:265 (1992). In addition, nicotine reportedly potentiates the pharmacological behavior of certain pharmaceutical compositions used for the treatment of certain disorders. See, Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Furthermore, various other beneficial pharmacological effects of nicotine have been proposed. See, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *JPET* 221:91–96 (1982); and Hamon, *Trends in Pharmacol. Res.* 15:36.

Various nicotinic compounds have been reported as being useful for treating a wide variety of conditions and disorders. See, for example, Williams et al. *DN&P* 7(4):205–227 (1994), Arneric et al., *CNS Drug Rev.* 1(1):1–26 (1995), Arneric et al., *Exp. Opin. Invest. Drugs* 5(1):79–100 (1996), Bencherif et al., *JPET* 279:1413 (1996), Lippiello et al., *JPET* 279:1422 (1996), Damaj et al., *Neuroscience* (1997), Holladay et al., *J. Med. Chem.* 40(28): 4169–4194 (1997), Bannon et al., *Science* 279: 77–80 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al. Nicotinic compounds are reported as being particularly useful for treating a wide variety of Central Nervous System (CNS) disorders.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic abnormality, a dopaminergic abnormality, an adrenergic abnormality and/or a serotonergic abnormality. CNS disorders of relatively common occurrence include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia, Tourette's syndrome and neuroendocrine disorders (e.g., obesity, bulemia and diabetes insipidus).

Nicotinic receptor antagonists have been used for the treatment of certain disorders. For example, mecamylamine has been marketed as Inversine by Merck & Co. Inc. as an antihypertensive agent; and trimethaphan has been marketed as Arfonad by Roche Laboratories as a vasodepressor agent. See, Goodman and Gilman's *The Pharmacological Basis of Therapeutics*, 6$^{th}$ Ed. p. 217 (1980). Nicotinic receptors have been implicated in convulsions, such as those that occur as a result of autosomal dominant nocturnal frontal lobe epilepsy. See, Steinlein et al., *Nat. Genet.* 11: 201–203 (1996). Nicotinic antagonists have been reported to inhibit viral infection. For example, nicotinic antagonists have been reported to inhibit the infection of dorsal root ganglion neurons by the rabies virus. See, Castellanos et al., *Neurosci. Lett.* 229: 198–200 (1997). Other uses for nicotinic antagonists have been proposed. See, for example, Popik et al., *JPET* 275: 753–760 (1995) and Rose et al., *Clin. Pharm. Ther.* 56(1): 86–9 (1994).

Derivatives of adamantane have been recognized as being antagonists at certain receptor subtypes. See, for example, Antonov et al., *Mol. Pharmacol.*, 47(3): 558–567 (1995) and Becker et al., *Bioorg. Med. Chem. Let.* 7(14): 1887–1890 (1997). Derivatives of adamantane also have been shown to exhibit antiviral properties. See, for example, Fytas et al., *Bioorg. Med. Chem. Let.* 7(17): 2149–2154 (1997); Skwarski et al., *Acta Poloniae Pharmaceutica*, 45: 391–394 (1988); Kreutzberger et al, *Archiv der Pharmazie*, 308: 748–754 (1975); Pellicciari et al., *Arzneimittel-Forshung* 30: 2103–2105 (1980); Danilenko et al., *Farma. Zhurnal*, 31: 36–40 (1976); and Beare et al., *Lancet* 1: 1039–1040 (1972). Derivatives of adamantane also have been shown to exhibit anti-bacterial properties. See, for example, Garoufalias et al., *Annales Pharmaceutiques Francaises*, 46: 97–104 (1988). Derivatives of adamantanes also have been reported as inhibitors of convulsions. See, Antonov et al., *Mol. Pharmacol.*, 47(3): 558–567 (1995). Derivatives of adamantane also have been proposed for the treatment of type II diabetes. See, Campbell, *Pharmacy Times* 53: 32–37, 39–40 (1987). Derivatives of adamantane also have been proposed to have a marked anorectic effect in mice. See, *Farmazo-Edizione Scientifica* 34: 1029–1038 (1979). Derivatives of adamantane also have been proposed be effective in the prevention of catalepsy in animal models. See, Vikhlyaev et al., *Pharm. Chem. J.* 14: 185–188 (1981).

It would be desirable to provide a useful method for the prevention and treatment of a conditon or disorder by administering a nicotinic compound to a patient susceptible to or suffering from such a disorder. It would be highly beneficial to provide individuals suffering from certain disorders with interruption of the symptoms of those disorders by the administration of a pharmaceutical composition containing an active ingredient having nicotinic pharmacology and providing a beneficial effect, but which does not provide any significant associated side effects (e.g., increased heart rate and blood pressure attendant with interaction of that compound with cardiovascular sites). It would be highly desirable to provide a pharmaceutical composition incorporating a compound that interacts with nicotinic receptors, but which composition does not significantly effect those receptor subtypes which have the potential to induce undesirable side effects (e.g., appreciable pressor cardiovascular effects and appreciable activity at skeletal muscle sites).

SUMMARY OF THE INVENTION

The present invention relates to 1-aza-2-(3-pyridyl)tricyclo[3.3.1.1$^{3,7}$]decanes. Representative compounds are 1-aza-2-(3-pyridyl)tricyclo[3.3.1.1$^{3,7}$]decane, 1-aza-2-[5-amino-(3-pyridyl)]tricyclo[3.3.1.1$^{3,7}$]decane, 1-aza-2-[5-ethoxy-(3-pyridyl)]tricyclo[3.3.1.1$^{3,7}$]decane, 1-aza-2-[5-isopropoxy-(3-pyridyl)]tricyclo[3.3.1.1$^{3,7}$]decane, 1-aza-2-[5-bromo-(3-pyridyl)]tricyclo[3.3.1.1$^{3,7}$]decane and 5-aza-6-[5-bromo-(3-pyridyl)]tricyclo[3.3.1.1$^{3,7}$]decan-2-ol.

The present invention also relates to methods for the prevention or treatment of conditions and disorders. The present invention also relates to methods for the prevention or treatment of conditions and disorders, including central nervous system (CNS) disorders, which are characterized by an alteration in normal neurotransmitter release. The methods involve administering to a subject an effective amount of a compound of the present invention.

The present invention, in another aspect, relates to a pharmaceutical composition comprising an effective amount of a compound of the present invention. Such a pharmaceutical composition incorporates a compound that, when employed in effective amounts, has the capability of interacting with relevant nicotinic receptor sites of a subject, and hence has the capability of acting as a therapeutic agent in the prevention or treatment of disorders characterized by an alteration in normal neurotransmitter release. Preferred pharmaceutical compositions comprise novel compounds of the present invention.

The compounds of the present invention are beneficial in therapeutic applications requiring a selective inhibition at certain nicotinic receptor subtypes; that is, the compounds are antagonists at certain nicotinic receptor subtypes. The pharmaceutical compositions of the present invention are useful for the prevention and treatment of a wide variety of conditions or disorders. The compounds of the present invention are useful for treating certain CNS conditions and disorders; such as in providing neuroprotection, in treating patients susceptible to convulsions, in treating depression, in treating autism, in treating certain neuroendocrine disorders, and in the management of stroke. The compounds of the present invention also are useful in treating hypertension, for effecting weight loss, in treating type II diabetes, or as anti-bacterial or antiviral agents. The compounds of the present invention also are useful, when appropriately radiolabeled, as probes in life science applications (e.g., as selective probes in neuroimaging applications).

The pharmaceutical compositions provide therapeutic benefit to individuals suffering from such conditions or disorders and exhibiting clinical manifestations of such conditions or disorders in that the compounds within those compositions, when employed in effective amounts, have the potential to (i) exhibit nicotinic pharmacology and affect relevant nicotinic receptors sites (e.g., act as a pharmacological antagonists at nicotinic receptors), and (ii) inhibit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) when employed in effective amounts do not cause appreciable adverse side effects (e.g., significant increases in blood pressure and heart rate, significant negative effects upon the gastro-intestinal tract, and significant effects upon skeletal muscle). The pharmaceutical compositions of the present invention are believed to be safe and effective with regards to prevention and treatment of various conditions or disorders.

The foregoing and other aspects of the present invention are explained in detail in the detailed description and examples set forth below.

DETAILED DESCRIPTION OF THE INVENTION

The present invention relates to compounds having the general formula I:

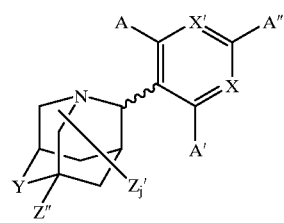

wherein each of X and X' are individually nitrogen or carbon bonded to a substituent species characterized as having a sigma m value greater than 0, often greater than 0.1, and generally greater than 0.2, and even greater than 0.3; less than 0, generally less than −0.1; or 0 (i.e., is hydrogen); as determined in accordance with Hansch et al., *Chem. Rev.* 91:165 (1991); Z' is a substituent other than hydrogen (e.g., alkyl, aryl, aralkyl, halo, hydroxyl, alkoxyl, alkylhydroxy, cyano and mercapto); j is an integer from 0 to 5, preferably 0 or 1, and most preferably 0; and the wavy line in the structure indicates that certain compounds can exist in the form of enantiomers or diastereomers depending upon the placement of substituent groups on the 1-aza-tricyclo[3.3.1.1$^{3,7}$]decane portion of the compound. The identity of A, A' and A" can vary, and individually represent those species described as substituent species to the aromatic carbon atom previously described for X and X'; and each of those substituent species often has a sigma m value between about −0.3 and about 0.75, frequently between about −0.25 and about 0.6. More specifically, individual examples of the substituent species to X and X' (when X and X' are carbon atoms), Z', A, A' and A" include F, Cl, Br, I, R', NR'R", CF$_3$, OH, CN, NO$_2$, C$_2$R', SH, SCH$_3$, N$_3$, SO$_2$CH$_3$, OR', SR', C(=O)NR'R", NR'C(=O)OR', C(=O)R', C(=O)OR', (CH$_2$)$_q$OR', OC(=O)R', OC(=O)NR'R", and NR'C(=O)OR', where R' and R" are individually hydrogen or lower alkyl (e.g., C$_1$–C$_{10}$ alkyl, preferably C$_1$–C$_6$ alkyl, and more preferably cyclohexyl, methyl, ethyl, isopropyl or isobutyl), an aromatic group-containing species, and q is an integer from 1 to 6. In certain circumstances, it is preferred that when X' is carbon, the sigma m value of the substituent bonded to that carbon is not equal to 0. However, for certain compounds, the sigma m value of A" is equal to 0; that is, A" is H. For certain preferred compounds, X' is carbon bonded to a non-hydrogen substituent (i.e., such compounds are 5-substituted-3-pyridyl compounds). In addition, it is highly preferred that A is hydrogen, it is preferred that A' is hydrogen, and normally A" is hydrogen. Generally, A and A' both are hydrogen; sometimes A and A' are hydrogen, and A" is halo, OR', OH, NR'R", SH or SR'; and often A, A' and A" are all hydrogen. R' and R" can be straight chain or branched alkyl, or R' and R" can form a cycloalkyl functionality (e.g., cyclopropyl, cyclobutyl, cyclopentyl, cyclohexyl, cycloheptyl, adamantyl, quinuclidinyl). Representative aromatic group-containing species include pyridinyl, quinolinyl, pyrimidinyl, phenyl, benzyl (where any of the foregoing can be suitably substituted with at least one substituent group, such as alkyl, halo, or amino substituents). Representative aromatic ring systems are set forth in Gibson et al., *J. Med. Chem.* 39:4065 (1996). For NR'R", the nitrogen and R' and R" can form a ring structure, such as aziridinyl, azetidinyl, pyrrolidinyl, piperidinyl, piperazinyl or morpholinyl. Z" includes hydrogen or Z' (where Z' is as previously defined), preferably hydrogen. Preferably, Z' is attached to either of the carbon atoms alpha to Y. Y includes C=O, C(OH)R', or CHA (where A is as previously defined), but preferably Y is $CH_2$. The compounds represented in general formula I are optically active; and can be provided and used in the form of racemates and enantiomers. In a particular embodiment, X' is nitrogen or carbon bonded to a substituent species characterized as having a sigma m value greater than 0, less than 0 or 0; X is nitrogen or carbon bonded to a substituent species characterized as having a sigma m value greater than 0, less than 0, but not equal to 0; A, A' and A" are individually substituent species characterized as having a sigma m value greater than 0, less than 0 or 0; Z' is a substituent other than hydrogen; j is an integer from 0 to 5; and the wavy line in the structure indicates that the compound can exist in the form of an enantiomer or a diasteromer; Z" is hydrogen or a substituent other than hydrogen; Y is C=O, C(OH)R' or CHA, where R' is hydrogen or lower alkyl.

A representative compound is 5-aza-1-(hydroxymethyl)-6-(3-pyridyl)tricyclo[$3.3.1.1^{3,7}$]-decan-2-one, where A, A' and A" each are hydrogen, X is CH, X' is nitrogen, Y is C=O, Z" is $CH_2OH$ and j is 0. Another representative compound is 5-aza-6-(3-pyridyl)tricyclo[$3.3.1.1^{3,7}$]decan-2-one, where A, A' and A" each are hydrogen, X is CH, X' is nitrogen, j is 0, Z" is H and Y is C=O. Another representative compound is 5-aza-6-(3-pyridyl)tricyclo[$3.3.1.1^{3,7}$]decan-2-ol, where A, A' and A" each are hydrogen, X is CH, X' is nitrogen, Y is $CH_2OH$, j is 0 and Z" is H. These compounds are particularly useful as intermediates for the preparation of other compounds of the present invention.

A representative compound of the present invention is 1-aza-2-(3-pyridyl)tricyclo[$3.3.1.1^{3,7}$]decane, where A, A' and A" each are hydrogen, X is CH, X' is nitrogen, Y is $CH_2$, j is 0, Z" is H and X is CH. Another representative compound of the present invention is 1-aza-2-(5-bromo(3-pyridyl))tricyclo[$3.3.1.1^{3,7}$]decane, where A, A' and A" each are hydrogen, X is CBr, X' is nitrogen, Y is $CH_2$, j is 0 and Z" is H. Another representative compound of the present invention is 1-aza-2-[5-amino-(3-pyridyl)]tricyclo[$3.3.1.1^{3,7}$]decane, where A, A' and A" each are hydrogen, X is $CNH_2$, X' is nitrogen, Y is $CH_2$, j is 0 and Z" is H. Another representative compound of the present invention is 1-aza-2-[5-ethoxy-(3-pyridyl)]tricyclo[$3.3.1.1^{3,7}$]decane, where A, A' and A" each are hydrogen, Y is $CH_2$, j is 0, Z" is H, X is $COCH_2CH_3$, and X' is nitrogen. Another representative compound of the present invention is 1-aza-2-[5-isopropoxy-(3-pyridyl)]tricyclo[$3.3.1.1^{3,7}$]decane, where A, A' and A" each are hydrogen, Y is $CH_2$, j is 0, Z" is H, X is $COC_3H_7$, and X' is nitrogen. Another representative compound of the present invention is 5-aza-6-[5-bromo-(3-pyridyl)]tricyclo[$3.3.1.1^{3,7}$]decan-2-ol, where A, A' and A" each are hydrogen, X is CBr, X' is nitrogen, Y is $CH_2OH$, j is 0 and Z" is H.

The manner in which 1-aza-2-(3-pyridyl)-tricyclo [$3.3.1.1^{3,7}$]decanes of the present invention can be synthetically produced is as follows. 3-aminopyridine, which is commercially available from the Aldrich Chemical Co., can be converted into the Schiff base, 2-aza-1,1-diphenyl-3-(3-pyridyl)-prop-1-ene, by reaction with benzophenone, according to the procedure described in U.S. Pat. No. 5,510,355 to Bencherif et al. the disclosure of which is incorporated herein in its entirety. This Schiff base is then reacted with the O-mesylate derivative of 1,4-dioxaspiro[4,5]decan-8-ol (which can be prepared according to the procedure of Braem et al., *Org. Mass Spectrom.*, 1982, 17(2), 102) in dry THF at −78° C. in the presence lithium diisopropylarnide, to afford the intermediate 8-[2-aza-3,3-diphenyl-1-(3-pyridyl)-prop-2-enyl]-1,4-dioxaspiro[4.5] decane. This intermediate is then treated with 2% $H_2SO_4$ and paraformaldehyde to afford a mixture of 5-aza-1-(hydroxymethyl)-6-(3-pyridyl)tricyclo[$3.3.1.1^{3,7}$]decane-2-one and 5-aza-6-(3-pyridyl)tricyclo-[$3.3.1.1^{3,7}$]decan-2-one. Fractionation of the mixture via silica gel chromatography affords pure samples of these two products. 5-Aza-1-(hydroxymethyl)-6-(3-pyridyl)tricyclo[$3.3.1.1^{3,7}$]decan-2-one was obtained as a mixture of diastereomers. Reduction of 5-aza-6-(3-pyridyl)tricyclo[$3.3.1.1^{3,7}$]decan-2-one with hydrazine and KOH in ethylene glycol, utilizing the general procedure described by Huang Minion (see ref. *J. Amer. Chem. Soc.*, 1946, 68, 2487), or by reacting the ketone with tosyl hydrazine, and treating the resulting tosyl hydrazide derivative with sodium cyanoborohydride, to afford 1-aza-2-(3-pyridyl)-tricyclo[$3.3.1.1^{3,7}$]decane.

5-Aza-6-(3-pyridyl)-tricyclo[$3.3.1.1^{3,7}$]decan-2-one can also be reduced with sodium borohydride in methanol, as described for the reduction of camphor in *Introduction to Organic Laboratory Techniques*, Second Edition, p 156, Saunders College Publishing Co., to afford 5-aza-6-(3-pyridyl)-tricyclo-[$3.3.1.1^{3,7}$]decan-2-ol as a mixture of chromatographically inseparable diastereomers.

The manner in which certain 5-substituted-3-pyridyl compounds of the present invention can be synthetically produced can vary. For example, 3-(5-bromo-3-pyridyl)-containing compounds can be prepared using a combination of synthetic techniques known in the art. 2-[3-(5-bromopyridiyl)]-substituted analogs of the 1-azatricyclo [$3.3.1.1^{3,7}$]decanes can all be prepared starting from 5-bromonicotinic acid, which is commercially available from Aldrich Chemical Co. The 5-bromonicotinic acid is converted to the mixed anhydride with ethyl chloroformate and reduced with lithium aluminum hydride/tetrahydrofuran (THF) at −78° C., to afford 5-bromo-3-hydroxymethylpyridine, as reported by Ashimori et al., *Chem. Pharm. Bull.* 38:2446 (1990). Alternatively, the 5-bromonicotinic acid is esterified in the presence of sulfuric acid and ethanol, and the intermediate ester is reduced with sodium borohydride to yield 5-bromo-3-hydroxymethylpyridine, according to the techniques reported in C. F. Natatis, et al., *Org. Prep. and Proc. Int.*

24:143 (1992). The resulting 5-bromo-3-hydroxymethylpyridine can then be converted to the 5-bromo-3-aminomethylpyridine utilizing a modification of the techniques of O. Mitsunobu, *Synthesis* 1 (1981), or via treatment of 5-bromo-3-hydroxymethylpyridine with thionyl chloride and reaction of the resulting 5-bromo-3-chloromethylpyridine with aqueous ammonia/ethanol, according to North et al., WO 95/28400. 5-Bromo-3-aminomethylpyridine can be converted to 1-aza-2-[5-bromo-(3-pyridyl)]tricyclo[3.3.1.1$^{3,7}$]decane using procedures analogous to those described hereinbefore for the preparation of 1-aza-2-(3-pyridyl)tricyclo[3.3.1.1$^{3,7}$]decane.

The manner in which the 5-bromo-3-pyridyl analogs 1-aza-2-(3-pyridyl)tricyclo[3.3.1.1$^{3,7}$]decanes of the present invention can be synthetically prepared is analogous to the synthesis of the corresponding unsubstituted parent compounds described hereinbefore, except that 5-bromo-3-aminomethylpyridine (see, U.S. patent application Ser. No. 08/885,397, filed Jun. 30, 1997, the disclosure of which is incorporated herein by reference in its entirety) is utilized instead of 3-aminomethylpyridine, in the formation of the Schiff base, 2-aza-1,1-diphenyl-3-[3-(5-bromopyridyl)]-prop-1-ene, from the reaction with benzophenone, as described in U.S. patent application Ser. No. 08/885,397, filed Jun. 30, 1997. Thereafter, the 5-bromo Schiff base is subjected to the same procedures as described for the preparation of the unsubstituted parent compounds.

A number of analogs substituted at C-5 of the pyridine ring in the aforementioned compounds can be prepared from the corresponding 5-bromo compound. For example, 5-amino substituted compounds and 5-alkylamino substituted compounds can be prepared from the corresponding 5-bromo compound using the general techniques described in C. Zwart, et al., *Recueil Trav. Chim. Pays-Bas* 74:1062 (1955). 5-Alkoxy substituted analogues can be prepared from the corresponding 5-bromo compound using the general techniques described in D. L. Comins, et al., *J. Org. Chem.* 55:69 (1990) and H. J. Den Hertog et al., *Rec. Trav. Chim. Pays-Bas* 74:1171 (1955). 5-Ethynyl-substituted compounds can be prepared from the appropriate 5-bromo compound using the general techniques described in N. D. P. Cosford et al., *J. Med. Chem.* 39:3235 (1996). The 5-ethynyl analogues can be converted into the corresponding 5-ethenyl, and subsequently the corresponding 5-ethyl analogues by successive catalytic hydrogenation reactions using techniques known to those skilled in the art of organic synthesis. 5-Azido substituted analogues can be prepared from the corresponding 5-bromo compound by reaction with sodium azide in dimethylforrnamide using techniques known in the art of organic synthesis. 5-Alkylthio substituted analogues can be prepared from the corresponding 5-bromo compound by reaction with an appropriate alkylmercaptan in the presence of sodium using techniques known to those skilled in the art of organic synthesis.

A number of 5-substituted analogs of the aforementioned compounds can be synthesized from the corresponding 5-amino compounds via the intermediate 5-diazonium salts. Among the other 5-substituted analogs that can be produced from intermediate 5-diazonium salts are: 5-hydroxy analogues, 5-fluoro analogues, 5-chloro analogues, 5-bromo analogues, 5-iodo analogues, 5-cyano analogues, and 5-mercapto analogues. These compounds can be synthesized using the general techniques set forth in Zwart et al., supra. For example, 5-hydroxy substituted analogues can be prepared from the reaction of the corresponding intermediate 5-diazonium salts with water. The 5-fluoro substituted analogues can be prepared from the reaction of the intermediate 5-diazonium salts with fluoroboric acid. The 5-chloro substituted analogues can be prepared from the reaction of the 5-amino compound with sodium nitrite and hydrochloric acid in the presence of copper chloride. The 5-cyano substituted analogues can be prepared from the reaction of the corresponding intermediate 5-diazonium salt with potassium copper cyanide. The 5-amino substituted analogues can also be converted to the corresponding 5-nitro analogue by reaction with fuming sulfuric acid and peroxide, according to the general techniques described in Y. Morisawa, *J. Med. Chem.* 20:129 (1977) for converting an arninopyridine to a nitropyridine. Appropriate intermediate 5-diazonium salts can also be used for the synthesis of mercapto substituted analogues using the general techniques described in J. M. Hoffman et al., *J. Med. Chem.* 36:953 (1993). The 5-mercapto substituted analogues can in turn be converted to the 5-alkylthio substituted analogues by reaction with sodium hydride and an appropriate alkyl bromide using techniques known to those skilled in the art of organic synthesis. The 5-acylamido analogues of the aforementioned compounds can be prepared by reaction of the corresponding 5-amino compounds with an appropriate acid anhydride or acid chloride using techniques known to those skilled in the art of organic synthesis.

The 5-hydroxy substituted analogues of the aforementioned compounds can be used to prepare corresponding 5-alkanoyloxy substituted compounds by reaction with the appropriate acid, acid chloride, or acid anhydride, using techniques known to those skilled in the art of organic synthesis.

The 5-cyano substituted analogues of the aforementioned compounds can be hydrolyzed using techniques known to those skilled in the art of organic synthesis to afford the corresponding 5-carboxamido substituted compounds. Further hydrolysis results in formation of the corresponding 5-carboxylic acid substituted analogues. Reduction of the 5-cyano substituted analogues with lithium aluminum hydride yields the corresponding 5-aminomethyl analogue.

The 5-acyl substituted analogues can be prepared from corresponding 5-carboxylic acid substituted analogues by reaction with an appropriate alkyl lithium using techniques known to those skilled in the art.

The 5-carboxylic acid substituted analogues of the aforementioned compounds can be converted to the corresponding ester by reaction with an appropriate alcohol, according to methods known in the art of organic synthesis. Compounds with an ester group at the 5-pyridyl position can be reduced with sodium borohydride or lithium aluminum hydride using techniques known in the art of organic synthesis, to produce the corresponding 5-hydroxymethyl substituted analogue. These analogues in turn can be converted to compounds bearing an ether moiety at the 5-pyridyl position by reaction with sodium hydride and an appropriate alkyl halide, using conventional techniques. Alternatively, the 5-hydroxymethyl substituted analogues can be reacted with tosyl chloride to provide the corresponding 5-tosyloxymethyl analogue. The 5-carboxylic acid substituted analogues can also be converted to the corresponding 5-alkylaminoacyl analogue by reaction with an appropriate alkylamine and thionyl chloride, using techniques known to those skilled in the art. The 5-acyl substituted analogues of the aforementioned compounds can be prepared from the reaction of the appropriate 5-carboxylic acid substituted compound with an appropriate alkyl lithium salt, using techniques known to those skilled in the art of organic synthesis.

The 5-tosyloxymethyl substituted analogues of the aforementioned compounds can be converted to the corresponding 5-methyl substituted compounds by reduction with lithium aluminum hydride, using techniques known to those skilled in the art of organic synthesis. 5-Tosyloxymethyl substituted analogues of the aforementioned compounds can also be used to produce 5-alkyl substituted compounds via reaction with an alkyl lithium salt using techniques known to those skilled in the art of organic synthesis.

The 5-hydroxy substituted analogues of the aforementioned compounds can be used to prepare 5-N-alkylcarbamoyloxy substituted compounds by reaction with N-alkylisocyanates using techniques known to those skilled in the art of organic synthesis. The 5-amino substituted analogues of the aforementioned compounds can be used to prepare 5-N-alkoxycarboxamido substituted compounds by reaction with alkyl chloroformate esters, using techniques known to those skilled in the art of organic synthesis.

Analogous chemistries to the ones described hereinbefore for the preparation of the 5-substituted analogues of the azatricyclo analogues can be devised for the synthesis of 2-, 4-, and 6-substituted analogues, utilizing the appropriate 2-, 4-, or 6-aminopyridyl intermediate, followed by diazotization to the corresponding diazoniurn salt, and then utilizing the same procedures for introducing the variety of substituents into the pyridine ring as was described for the 5-substituted analogues above. Similarly, by utilizing 2, 4- or 6-bromopyridyl derivatives of the above azatricyclo analogues, and subjecting each of these derivatives to the same procedures as described for introducing 5-substituents into the pyridyl ring from appropriate 5-bromo precursors of these azatricyclo analogues, additional 2-, 4- or 6-substituents can be obtained in the manner described above.

Chiral auxiliary reagents that have been reported in the literature can be utilized in the synthesis of the pure enantiomers of the aforementioned 1-aza-2-(3-pyridyl)-tricyclo $[3.3.1.1^{3,7}]$decanes, 1-aza-2-[5-amino-(3-pyridyl)]tricyclo $[3.3.1.1^{3,7}]$decanes, 1-aza-2-[5-ethoxy-(3-pyridyl)]tricyclo $[3.3.1.1^{3,7}]$decanes, 1-aza-2-[5-isopropoxy-(3-pyridyl)] tricyclo$[3.3.1.1^{3,7}]$decanes, 1-aza-2-[5-bromo-(3-pyridyl)] tricyclo$[3.3.1.1^{3,7}]$decanes and 5-aza-6-[5-bromo-(3-pyridyl)]tricyclo$[3.3.1.1^{3,7}]$decan-2-ols. D. Enders and U. Reinhold, *Liebigs Ann.* 11 (1996); D. Enders and D. L. Whitehouse, *Synthesis* 622 (1996)). One approach can be carried out using (+)-2-amino-3-phenylethanol (or its (−)-enantiomer), which is reacted with an appropriately substituted 3-pyridine carboxaldehyde in the presence of an optically pure amino acid as a chiral auxiliary agent, followed by treatment with the required pyrano magnesium bromide reagent and N-deprotection (via hydrogenolysis), to afford the chirally pure pyrano precursors of the aforementioned azatricyclo compounds. A second alternative method is the use of the chiral auxiliary agent, (S)-1-amino-2-methyloxymethylpyrrolidine (SAMP) or (S)-1-amino-2-(1-methoxy-1-methylethyl)-pyrrolidine (SADP), or their respective R-isomers, by reaction with an appropriately substituted 3-pyridine carboxaldehyde to form the corresponding oxime. Treatment of the oxime with the required dioxaspiro[4,5]decyl magnesium bromide, followed by deprotection with sodium/liquid ammonia will afford the appropriate chirally pure pyrano precursor of the aforementioned azatricyclo compounds. A third alternative method is the use of (+) or (−)-α-pinanone in place of benzophenone in the formation of the appropriate precursor Schiff base used in the synthesis of the aforementioned azatricyclo compounds. See, the types of chemistries disclosed in U.S. Pat. No. 5,510,355 to Bencherifet al. For example, (+)-α-pinanone is reacted with an appropriately substituted 3-aminomethylpyridine to form the corresponding Schiff base, which is then utilized in place of the corresponding N-diphenyhnethylidene-3-aminomethylpyridine, by reaction with the requisite dioxaspiro[4,5]decane-8-methane sulfonate or dioxaspiro[4,5]decane-8-halide intermediate in the presence of LDA, followed by N-deprotection in $NH_2OH$/acetic acid, to afford the appropriate chirally pure pyrano precursor of the aforementioned azatricyclo compounds.

In the case of the 2-substituted 1-azatricyclo$[3.3.1.1^{3,7}]$ decanes, use of the above enantioselective synthetic procedures will generate isomers with defined stereochemistry at C-2 of the 1-aza-2-(3-pyridyl)-tricyclo$[3.3.1.1^{3,7}]$decane ring.

The present invention relates to nicotinic antagonists. The present invention also relates to methods for providing prevention or treatment of conditions or disorders in a subject susceptible to such a condition or disorder, and for providing treatment to a subject suffering from a condition or disorder. For example, the method comprises administering to a patient an amount of a compound effective for providing some degree of prevention of the progression of a disorder such as a CNS disorder (i.e., provide protective effects), amelioration of the symptoms of the disorder, and/or amelioration of the reoccurrence of the disorder. In particular, the methods of the present invention comprise administering to a patient in need thereof, an amount of a compound selected from the group of compounds of general formula I hereinbefore, which amount is effective to prevent or treat the condition or disorder affecting the patient. The present invention further relates to pharmaceutical compositions incorporating the compounds of general formula I above.

The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, salicylate, p-toluenesulfonate, and ascorbate; salts with acidic amino acids such as aspartate and glutamate; alkali metal salts such as sodium salt and potassium salt; alkaline earth metal salts such as magnesium salt and calcium salt; ammonium salt; organic basic salts such as trimethylamine salt, triethylanine salt, pyridine salt, picoline salt, dicyclohexylamine salt, and N,N-dibenzylethylenediamine salt; and salts with basic amino acids such as the lysine salt and arginine salts. The salts may be in some cases be hydrates or ethanol solvates.

The compounds of the present invention are beneficial in therapeutic applications requiring a selective inhibition at certain nicotinic receptor subtypes; that is, the compounds are antagonists at certain nicotinic receptor subtypes. The pharmaceutical compositions of the present invention are useful for the prevention and treatment of a wide variety of conditions or disorders. The compounds of the present invention are useful for treating certain CNS conditions and disorders; such as in providing neuroprotection, in treating patients susceptible to convulsions, in treating depression, in treating autism, in treating certain neuroendocrine disorders, and in the management of stroke. The compounds of the present invention also are useful in treating hypertension, for effecting weight loss, in treating type II diabetes, or as anti-bacterial or antiviral agents. The compounds of the present invention also are useful, when appropriately radiolabeled, as probes in life science applications (e.g., as selective probes in neuroimaging applications). For example, compounds of the present invention can be used to inhibit interaction of viral proteins with nicotinic receptors. See, Bracci et al., *FEBS Letters*. 311(2): 115–118 (1992). See also, for example, the types of conditions and disorders that are treated using nicotinic compounds, as set forth in PCT WO 94/08992 and PCT WO 96/31475, and U.S. Pat. Nos. 5,583,140 to Bencherif et al., 5,597,919 to Dull et al. and 5,604,231 to Smith et al.

The pharmaceutical compositions of the present invention can also include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al., the disclosure of which is incorporated herein by reference in its entirety); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that effect the functioning of the CNS. More specifically, in treating a CNS disorder administration preferably is such so as to optimize the effect upon those relevant receptor subtypes (e.g., those which have an effect upon the functioning of the CNS), while minimizing the effects upon receptor subtypes in muscle and ganglia. Other suitable methods for administering the compounds of the present invention are described in U.S. Pat. No. 5,604,231 to Smith et al., the disclosure of which is incorporated herein by reference in its entirety.

Compounds of the present invention bind to relevant receptors and, are antagonists (i.e., inhibit relevant receptor subtypes). Concentrations, determined as the amount of compound per volume of receptor-containing tissue, typically provide a measure of the degree to which that compound binds to and affects relevant receptor subtypes. The compounds of the present invention are selective in that at relevant concentrations (i.e., low concentrations) those compounds bind to, and have inhibitory effects upon, receptors associated with the release of neurotransmitters (e.g., dopamine, within the CNS).

The appropriate dose of the compound is that amount effective to prevent occurrence of the symptoms of the condition or disorder, or to treat some symptoms of the condition or disorder from which the patient suffers. By "effective amount", "therapeutic amount" or "effective dose" is meant that amount sufficient to elicit the desired pharmacological or therapeutic effects, thus resulting in effective prevention or treatment of the condition or disorder. Thus, when treating a CNS disorder, an effective amount of compound is an amount sufficient to pass across the blood-brain barrier of the subject, to bind to relevant receptor sites in the brain of the subject, and to inhibit relevant nicotinic receptor subtypes (e.g., inhibits neurotransmitter secretion, thus resulting in effective prevention or treatment of the disorder). Prevention of the condition or disorder is manifested by delaying the onset of the symptoms of the condition or disorder. Treatment of the condition or disorder is manifested by a decrease in the symptoms associated with the condition or disorder, or an amelioration of the reoccurrence of the symptoms of the condition or disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to inhibit relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where desired therapeutic effects are observed but below the amounts where muscular effects are observed.

Typically, the effective dose of compounds generally requires administering the compound in an amount of less than 1 ug/kg of patient weight. Often, the compounds of the present invention are administered in an amount from 10 ng to less than 1 ug/kg of patient weight, frequently between about 0.1 ug to less than 1 ug/kg of patient weight, and preferably between about 0.1 ug to about 0.5 ug/kg of patient weight. Compounds of the present invention can be administered in an amount of 0.3 to 0.5 ug/kg of patient weight. For compounds of the present invention that do not induce effects on muscle or ganglion-type nicotinic receptors at low concentrations, the effective dose is less than 50 ug/kg of patient weight; and often such compounds are administered in an amount from 0.5 ug to less than 50 ug/kg of patient weight. The foregoing effective doses typically represent that amount administered as a single dose, or as one or more doses administered over a 24 hour period.

For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 500, often does not exceed about 400, and frequently does not exceed about 300 ug/24 hr./patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds, which are useful in carrying out the present invention are generally greater than about 0, often are greater than about 0.5, and frequently are greater than about 1.5. The log P values of such typical compounds generally are less than about 4, often are less than about 3.5, and frequently are less than about 3.0. Log P values provide a measure of the ability of a compound to pass across a diffusion barrier, such as a biological membrane. See, Hansch, et al., *J. Med. Chem.* 11:1(1968).

The compounds useful according to the method of the present invention have the ability to bind to, and in most circumstances, cause inhibition of, nicotinic dopaminergic receptors of the brain of the patient. As such, such compounds have the ability to express nicotinic pharmacology, and in particular, to act as nicotinic antagonists. The receptor binding constants of typical compounds useful in carrying out the present invention generally exceed about 0.1 nM, often exceed about 1 nM, and frequently exceed about 10 nM. The receptor binding constants of such typical compounds generally are less than about 1 M, often are less than about 100 nM, and frequently are less than about 20 nM. Receptor binding constants provide a measure of the ability of the compound to bind to half of the relevant receptor sites of certain brain cells of the patient. See, Cheng, et al., *Biochem. Pharmacol.* 22:3099 (1973).

The compounds useful according to the method of the present invention have the ability to demonstrate a nicotinic function by effectively inhibiting neurotransmitter secretion from nerve ending preparations (i.e., synaptosomes). As such, such compounds have the ability to inhibit relevant neurons to release or secrete acetylcholine, dopamine, and other neurotransmitters. Generally, typical compounds useful in carrying out the present invention provide for the inhibition of dopamine secretion in amounts of at least one third, typically at least about 10 times less, frequently at least about 100 times less, and sometimes at least about 1,000 times less, than those required for activation of muscle or ganglion-type nicotinic receptors.

The compounds of the present invention, when employed in effective amounts in accordance with the method of the present invention, are selective to certain relevant nicotinic receptors, but do not cause significant activation of receptors associated with undesirable side effects at concentrations at least 10 times higher than those required for inhibition of dopamine release. By this is meant that a particular dose of compound resulting in prevention and/or treatment of a CNS disorder, is essentially ineffective in eliciting activation of certain ganglionic-type nicotinic receptors at concentration higher than 5 times, preferably higher than 100 times, and more preferably higher than 1,000 times, than those required for inhibition of dopamine release. This selectivity of certain compounds of the present invention against those receptors responsible for cardiovascular side effects is demonstrated by a lack of the ability of those compounds to activate nicotinic function of adrenal chromaffin tissue at concentrations at least 10 times greater than those required for inhibition of dopamine release.

The compounds of the present invention, when employed in effective amounts in accordance with the method of the present invention, are effective towards providing some degree of prevention of the progression of certain conditions and disorders, amelioration of the symptoms of those conditions and disorders, an amelioration to some degree of the reoccurrence of those conditions and disorders. However, such effective amounts of those compounds are not sufficient to elicit any appreciable side effects, as demonstrated by increased effects relating to the cardiovascular system, and effects to skeletal muscle. As such, administration of certain compounds of the present invention provides a therapeutic window in which treatment of certain conditions and disorders is provided, and side effects are avoided. That is, an effective dose of a compound of the present invention is sufficient to provide the desired effects upon relevant nicotinic receptor subtypes, but is insufficient (i.e., is not at a high enough level) to provide undesirable side effects. Preferably, effective administration of a compound of the present invention resulting in treatment of a wide variety of conditions and disorders occurs upon administration of less than ⅕, and often less than ¹⁄₁₀ that amount sufficient to cause any side effects to a significant degree.

The following examples are provided to further illustrate the present invention, and should not be construed as limiting thereof.

EXAMPLES

Example 1

Determination of Log P Value:

Log P values, which have been used to assess the relative abilities of compounds to pass across the blood-brain barrier (Hansch, et al., *J. Med. Chem.* ii:1 (1968)), were calculated according using the Cerius$^2$ software package Version 3.0 by Molecular Simulations, Inc.

Example 2

Determination of Binding to Relevant Receptor Sites

Binding of the compounds to relevant receptor sites was determined in accordance with the techniques described in U.S. Pat. No. 5,597,919 to Dull et al. Inhibition constants (Ki values), reported in nM, were calculated from the IC$_{50}$ values using the method of Cheng et al., *Biochem, Pharmacol.* 22:3099 (1973).

Example 3

Determination of Receptor Activation/Inhibition and Dopamine Release

Dopamine release was measured using the techniques described in U.S. Pat. No. 5,597,919 to Dull et al. Release is expressed as a percentage of release obtained with a concentration of (S)-(−)-nicotine resulting in maximal effects. Reported EC$_{50}$ values are expressed in nM, and E$_{max}$ values represent the amount released relative to (S)-(−)-nicotine or tetramethylammonium ion (TMA), on a percentage basis.

Isotopic rubidium release was measured using the techniques described in Bencherif et al., *JPET*, 279: 1413–1421 (1996). Reported EC$_{50}$ values are expressed in nM, and E$_{max}$ values represent the amount of rubidium ion released relative to 300 uM tetranmethylammonium ion, on a percentage basis.

Reported IC$_{50}$ values are expressed in nM and represent the concentration resulting in 50% inhibition of agonist induced receptor activation. E$_{max}$ values represent the amount released relative to (S)-(−)-nicotine on a percentage basis.

Example 4
Determination of Interaction with Muscle Receptors

The determination of the interaction of the compounds with muscle receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis.

Example 5
Determination of Interaction with Ganglion Receptors

The determination of the interaction of the compounds with ganglionic receptors was carried out in accordance with the techniques described in U.S. Pat. No. 5,597,919 to Dull et al. The maximal activation for individual compounds ($E_{max}$) was determined as a percentage of the maximal activation induced by (S)-(−)-nicotine. Reported $E_{max}$ values represent the amount released relative to (S)-(−)-nicotine on a percentage basis.

Example 6

Sample No. 1 is 1-aza-2-(3-pyridyl)-tricyclo[$3.3.1.1^{3,7}$]decane, which was prepared in accordance with the following techniques:

1,4-Dioxaspiro[4,5]decan-8-methanesulfonate: Methanesulfonyl chloride (12 mmol, 0.92 mL) was added to the flask containing 1,4-dioxaspiro[4,5]decan-8-ol (10 mmol, 1.58 g, (prepared essentially according to the procedure of Braem, et al., *Org. Mass. Spectrom.*, 1982, 17(2), 102.) in tetrahydrofuran (THF)(20 mL) and triethylamine (15 mmol, 2.1 mL) at 0° C. under a nitrogen atmosphere. The reaction mixture was stirred overnight during which time a saturated aqueous solution of $NaHCO_3$ (15 mL) was added to the reaction mixture followed by extractions with diethyl ether (3×15 mL). The combined organic extracts were dried over anhydrous $MgSO_4$. Filtration, followed by concentration on a rotary evaporator yielded the mesylate as a pale yellow solid (2.26 g), which was used in the next step without any further purification.

5-Aza-6-(3-pyridyl)-tricyclo[$3.3.1.1^{3,7}$]decan-2-one: LDA (8.0 mmol) was generated at 0° C. by adding n-BuLi (3.40 mL of 2.35 M solution in hexane, 8.0 mmol) to a solution of diisopropylarnine (1.40 mL, 10.0 mmol) in dry THF (10.0 mL). The Schiff base, 2-aza-1,1-diphenyl-3-(pyridyl)prop-2-ene, formed from the reaction of 3-aminomethyl pyridine with benzophenone (2.18 g, 8.0 mmol; prepared using the method described in U.S. Pat. No. 5,510,355 to Bencherif et al.) was dissolved in dry THF (10.0 mL) and the solution cooled to −78° C. under a nitrogen atmosphere. LDA was then transferred to the solution of the Schiff base, using a double tipped needle under a positive nitrogen atmosphere. The resulting purple suspension was stirred for a further 45 minutes, during which time the temperature of the reaction mixture was allowed to rise to −45° C.

The mesylate of 1,4-dioxaspiro[4,5]decan-8-ol (2.26 g, 8.5 mmol) in THF (5.0 mL) was then added via a syringe and the reaction mixture was allowed to warm to ambient temperature followed by additional stirring for 12 hours. A saturated solution of $NaHCO_3$ in water (25 mL) was then added to the reaction mixture followed by extraction with EtOAc (3×20 mL). The combined organic extracts were dried over $K_2CO_3$, filtered and concentrated on a rotary evaporator. Precipitation was observed while the solvent was being evaporated. The residue obtained was resuspended in ethyl acetate (25 mL), filtered and concentrated on a rotary evaporator to obtain the alpha-substituted Schiff base as a yellow oil (3.87 g), which was contaminated by the starting Schiff base, in 34% yield. This unstable product was used in the next step without further purification as follows: The crude product in ethanol (absolute, 5.0 ml) was added to a gently boiling solution of paraformaldehyde (1.12 g) in $H_2SO_4$ (2% aq., 160 mL) over 45 minutes. The reaction mixture was refluxed for 24 hours, cooled to ambient temperature and then extracted with ethyl acetate (4×20 mL) to remove benzophenone. The aqueous portion was then neutralized with solid $K_2CO_3$ followed by basification with NaOH (15% aq. solution). Extraction with chloroform (4×25 mL), drying the combined organic extracts over anhydrous $K_2CO_3$, followed by removal of solvents on a rotary evaporator yielded a sticky solid which was essentially a mixture of 5-aza-1-(hydroxymethyl)-6-(3-pyridyl)tricyclo[$3.3.1.1^{3,7}$]decan-2-one and 5-aza-6-(3-pyridyl)tricyclo[$3.3.1.1^{3,7}$]decan-2-one (1.42 g), which was purified via silica gel column chromatography using ethyl acetate as the eluent ($R_f$=0.51, solvent: ethyl acetate). 5-Aza-1-(hydroxymethyl)-6-(3-pyridyl)tricyclo[$3.3.1.1^{3,7}$]decan-2-one (20 mg, $R_f$=0.31, solvent: ethyl acetate) was isolated as a mixture of diastereoisomers from the previous chromatographic procedure, and could not be separated by further silica gel column chromatography. 5-Aza-6-(3-pyridyl)tricyclo [$3.3.1.1^{3,7}$]decan-2-one was separated from the above crude product by silica gel column chromatography using ethyl acetate as the eluent ($R_f$=0.48, solvent: ethyl acetate) to afford a pale yellow solid (430 mg), which was further purified by crystallization using ethyl acetate and hexane.

1-Aza-2-(3-pyridyl)tricyclo[$3.3.1.1^{3,7}$]decane: This compound was prepared from 5-aza-6-(3-pyridyl)tricyclo [$3.3.1.1^{3,7}$]decan-2-one essentially in accordance with the general reduction procedure described by Huang-Minion (see ref. *J. Am. Chem. Soc.*, 1946, 68, 2487) as follows: Hydrazine (0.5 mmol, 16 uL) was added to a mixture of 5-aza-6-(3-pyridyl)tricyclo[$3.3.1.1^{3,7}$]decan-2-one (0.25 mmol, 57 mg) and potassium hydroxide (0.84 mmol, 470 mg) in diethylene glycol (1 ml). The reaction mixture was then heated at 190° C. for one hour with a condenser attached to the reaction flask and finally for the two hours at 200° C. without the condenser. After cooling to ambient temperature the contents of the flask were poured in water (10 mL) and then extracted with ethyl acetate (3×5 mL). Combined organic extracts were dried over $K_2CO_3$ and finally concentrated on a rotary evaporator to obtain 68 mg of a brown oil. Purification by silica gel column chromatography using methanol (10% v/v) in chloroform as the eluent ($R_f$=0.36, solvent system: chloroform:methanol, 90:10) yielded the product (11 mg) as a pale yellow oil.

The compound exhibits a log P of 2.632, and such a favorable log P value indicates that the compound has the capability of passing the blood-brain barrier. The compound exhibits a Ki of 15 nM. The low binding constant indicates that the compound exhibits good high affinity binding to certain CNS nicotinic receptors. With regards to dopamine release, the compound exhibits an $IC_{50}$ value of −695 nM and an $E_{max}$ value of 0%, indicating that the compound is an antagonist at relevant receptor subtypes. The compound exhibits an $E_{max}$ of 21% at muscle-type receptors and an $E_{max}$ of 27% at ganglia-type receptors, indicating a lack of potential side effects in subjects receiving administration of such a compound in relevant amounts.

Example 7

Sample No. 2 is 1-aza-2-[5-bromo(3-pyridyl)]tricyclo [$3.3.1.1^{3,7}$]decane, which was prepared in accordance with the following techniques:

5-Aza-6-(5-bromo(3-pyridyl))-3,3-diphenylprop-2-enyl)-1,4-dioxaspiro[4,5]decane: To a stirring solution of 2-aza-3-(5-bromo(3-pyridyl))-1,1-diphenylprop-1-ene (4.5 g, 12.9 mmol); prepared from the reaction of 3-aminomethyl-5-bromopyridine with benzophenone, using the methods set forth in U.S. patent application Ser. No. 08/885,397, filed Jun. 10, 1997, in tetrahydrofuran (100 ml) was added LDA (16.8 mmol) in tetrahydrofuran at −78° C. The reaction mixture was stirred at −78° C. for 1 hr, then 1,4-dioxaspiro [4,5]decan-8-methanesulfonate was added (3.3 g, 14.2 mmol) in tetrahydrofuran (25 ml) at −78° C. The reaction was continued for 18 hr at room temperature and quenched by adding 10 ml of aqueous saturated ammonium chloride solution. The reaction mixture was poured into aqueous saturated sodium bicarbonate solution, extracted with chloroform (2×150 mL) and the combined organic liquors dried over anhydrous sodium sulfate. Removal of solvents under reduced pressure yielded the title compound in crude form as a pale brown colored oil. This crude product was used in the next reaction without further purification.

5-Aza-6-(5-bromo(3-pyrridyl))tricyclo[3.3.1.1$^{3,7}$]decane-2-one: To a gently boiling solution of paraformaldehyde (1.2 g) in 2% aqueous sulfuric acid was slowly added a solution of the above crude 5-aza-6-(5-bromo(3-pyridyl))-3,3-diphenylprop-2-enyl)-1,4-dioxaspiro[4,5]decane in ethyl alcohol (15 ml). The reaction mixture was refluxed for 18 hr, cooled to room temperature and extracted with ethyl acetate (2×100 ml). The aqueous phase was separated, basified to pH 14 by adding 20% aqueous sodium hydroxide to the aqueous solution contained in an ice bath, and extracted with chloroform (3×300 mL). The combined organic layers were dried over anhydrous sodium sulfate, filtered and evaporated to dryness under reduced pressure. Purification of the resulting brown colored oil by silica gel column chromatography using ethyl acetate as the mobile phase, gave 306 mg (12%, 2 steps) of the title compound as a pale yellow colored oil.

((5-Aza-6-(5-bromo(3-pyridyl))tricyclo[3.3.1.1$^{3,7}$]dec-2-ylidene)methylamino)((4-methylphenyl)sulfonyl)amine: 5-Aza-6-(5-bromo-(3-pyridyl))tricyclo[3.3.1.1$^{3,7}$]decane-2-one (98 mg ; 32 μmol) was dissolved in methyl alcohol (5 mL), then p-toluenesulfonylhydrazine (74 mg) and a catalytic amount of p-toluenesulfonic acid monohydrate were added. The reaction mixture was stirred at ambient temperature overnight, then poured into saturated aqueous sodium bicarbonate solution (30 ml) and the resulting mixture extracted with chloroform (2×30 mL). The organic layers were separated, combined, washed with brine, dried over anhydrous sodium sulfate and filtered. After removal of the solvent under reduced pressure, purification of the oily residue was carried out by silica gel column chromatography utilizing ethyl acetate-hexane (1:2) as mobile phase, to yield 109 mg (69%) of the title compound.

1-Aza-2-(5-bromo(3-pyridyl))tricyclo[3.3.1.1$^{3,7}$]decane: A mixture of 5-aza-6-[5-bromo(3-pyridyl)]tricyclo[3.3.1.1$^{3,7}$] dec-2-ylidene)-methylamino)((4-methylphenyl)sulfonyl) amine (100 mg, 0.21 mmol), sodium cyanoborohydride (66 mg, 1.05 mmol) and catalytic amount of of p-toluenesulfonic acid monohydrate in ethyl alcohol (10 ml) was refluxed for 6 hr. The mixture was then cooled in an ice bath, and extracted with chloroform (2×40 ml). The combined organic extracts were dried over anhydrous magnesium sulfate and filtered. After removal of solvent under reduced pressure, purification of the oily residue was carried out by silica gel column chromatography utilizing chloroform-acetone (4:1) as the mobile phase, to yield 40 mg (64%) of the title compound.

The compound exhibits a log P of 2.768, and such a favorable log P value indicates that the compound has the capability of passing the blood-brain barrier. The compound exhibits a Ki of 2 nM. The low binding constant indicates that the compound exhibits good high affinity binding to certain CNS nicotinic receptors. With regards to dopamine release, the compound exhibits an $EC_{50}$ value of greater than 100,000 nM and an $E_{max}$ value of 0%, indicating that the compound is not effective at inducing neurotransmitter release even at very high concentrations. With regards to rubidium ion release, the compound exhibits an $EC_{50}$ value of greater than 100,000 nM and an $E_{max}$ value of 0%, indicating that the compound is not effective at inducing activation of CNS nicotinic receptors, even at high concentrations. The compound exhibits an $E_{max}$ of 32% at muscle-type receptors and an $E_{max}$ of 50% at ganglia-type receptors, indicating a lack of potential side effects in subjects receiving administration of such a compound in relevant amounts.

Example 8

Sample No. 3 is 1-aza-2-[5-amino-(3-pyridyl)]tricyclo [3.3.1.1$^{3,7}$]decane trihydrochloride, which was prepared in accordance with the following methodology:

1-Aza-2-[5-amino(3-pyridyl)]tricyclo[3.3.1.1$^{3,7}$]decane trihydrochloride: To a solution of 1-aza-2-[5-bromo(3-pyridyl)]tricyclo[3.3.1.1$^{3,7}$]decane (365 mg, 1.25 mmol) in ethanol (4 mL) and aqueous ammonia (10 mL, 0.88 s.g.) was added copper sulfate (300 mg). The mixture was heated at 155° C. overnight in a sealed tube. The reaction mixture was then cooled, extracted with chloroform (3×50 mL), and the combined organic extracts were washed with brine (50 mL). The organic layer was separated, dried over anhydrous magnesium sulfate, and evaporated to dryness. The product was dissolved in a mixture of methanol (2 mL) and conc. hydrochloric acid (2 mL) and the solution was evaporated to dryness on a rotary evaporator. The resulting solid was dissolved in methanol (1 ml) and was crystallized by careful addition of dry diethyl ether. The product was filtered at the pump and dried under vacuum, to afford the title compound (210 mg, 50%) as a white crystalline solid.

The compound exhibits a log P of 1.159, and such a favorable log P value indicates that the compound has the capability of passing the blood-brain barrier. The compound exhibits a Ki of 44 nM. The low binding constant indicates that the compound exhibits good high affinity binding to certain CNS nicotinic receptors. With regards to dopamine release, the compound exhibits an $EC_{50}$ value of greater than 100,000 nM and an $E_{max}$ value of 0%, indicating that the compound is not effective at inducing neurotransmitter release even at very high concentrations. With regards to rubidium ion release, the compound exhibits an $EC_{50}$ value of greater than 100,000 nM and an $E_{max}$ value of 0%, indicating that the compound is not effective at inducing activation of CNS nicotinic receptors, even at high concentrations. The compound exhibits an $E_{max}$ of 75% at muscle-type receptors and an $E_{max}$ of 17% at ganglia-type receptors, indicating a lack of potential side effects in subjects receiving administration of such a compound in relevant amounts.

Example 9

Sample No. 4 is 1-aza-2-[5-ethoxy-(3-pyridyl)]-tricyclo-[3.3.1.1$^{3,7}$]decane, which was prepared in accordance with the following methodology:

1-Aza-2-[5-ethoxy-(3-pyridyl)]-tricyclo[3.3.1.1$^{3,7}$]decane: To a stirred solution of 2-[5-amino-(3-pyridyl)]tricyclo [3.3.1.1$^{3,7}$] trihydrochloride (65 mg, 0.19 mmol) in dry ethanol (9 mL) was added isoamyl nitrite ( 0.4 mL, 3.0 mmol) and the mixture was refluxed for 2 h. When TLC of the reaction mixture showed absence of starting material, the heating was stopped, and the mixture was allowed to cool to ambient temperature; the solvent was removed on a rotary evaporator to yield a brown oil. The product was dissolved in water (10 mL) and saturated aqueous sodium bicarbonate (10 ml), and the resulting mixture was extracted with chloroform (3×30 mL), the combined organic liquors dried over anhydrous sodium sulfate, and evaporated to dryness under reduced pressure. Purification of the crude oily product by silica gel column chromatography (methanol: chloroform; 5:95) yielded the title compound (25 mg, 48%) as a pale yellow oil, which solidified on refrigeration at 4° C.

The compound exhibits a log P of 3.491, and such a favorable log P value indicates that the compound has the capability of passing the blood-brain barrier. The compound exhibits a Ki of 1.0 nM. The low binding constant indicates that the compound exhibits good high affinity binding to certain CNS nicotinic receptors. With regards to dopamine release, the compound exhibits an $EC_{50}$ value of greater than 100,000 nM and an $E_{max}$ value of 0%, indicating that the compound is not effective at inducing neurotransmitter release even at very high concentrations. In addition, with regards to dopamine release, the compound exhibits an $IC_{50}$ value of 846 nM, indicating that the compound is an antagonist at relevant receptor sites. With regards to rubidium ion release, the compound exhibits an $EC_{50}$ value of greater than 100,000 nM and an $E_{max}$ value of 0%, indicating that the compound is not effective at inducing activation of CNS nicotinic receptors, even at high concentrations. In addition, with regards to the rubidium ion release assay, the compound exhibits an $IC_{50}$ value of 630 nM, indicating that the compound is an antagonist at relevant receptor sites. The compound exhibits an $E_{max}$ of 22% at muscle-type receptors and an $E_{max}$ of 0% at ganglia-type receptors, indicating a lack of potential side effects in subjects receiving administration of such a compound in relevant amounts.

Example 10

Sample No. 5 is 1-aza-2-[5-isopropoxy-(3-pyridyl)]tricyclo[3.3.1.1$^{3,7}$]decane, which was prepared in accordance with the following methodology:

1-Aza-2-[5-isopropoxy(3-pyridyl)]tricyclo[3.3.1.1$^{3,7}$]decane: Isoamyl nitrite (0.4 mL, 3.0 mmol) was added to a stirred solution of 2-[5-amino-(3-pyridiyl)]tricyclo[3.3.1.1$^{3,7}$]trihydrochloride (65 mg, 0.19 mmol) in dry isopropanol (9 mL) and the mixture was refluxed for 2 h. When TLC of the reaction mixture showed absence of starting material, the heating was stopped and the mixture was allowed to cool to ambient temperature; the solvent was removed on a rotary evaporator to yield a brown colored oil. The product was dissolved in water (10 mL) and saturated aqueous sodium bicarbonate (10 mL), extracted with chloroform (3×30 ml), and the combined organic liquors dried over anhydrous sodium sulfate and evaporated to dryness under reduced pressure. Purification of the crude product by silica gel column chromatography (methanol:chloroform; 5:95), yielded the title compound (35 mg, 67%) as pale yellow oil.

The compound exhibits a log P of 4.036, and such a favorable log P value indicates that the compound has the capability of passing the blood-brain barrier. The compound exhibits a Ki of 24 nM. The low binding constant indicates that the compound exhibits good high affinity binding to certain CNS nicotinic receptors. With regards to dopamine release., the compound exhibits an $EC_{50}$ value of greater than 100,000 nM and an $E_{max}$ value of 0%, indicating that the compound is not effective at inducing neurotransmitter release even at very high concentrations. With regards to rubidium ion release, the compound exhibits an $EC_{50}$ value of greater than 100,000 nM and an $E_{max}$ value of 0%, indicating that the compound is not effective at inducing activation of CNS nicotinic receptors, even at high concentrations. The compound exhibits an $E_{max}$ of 114% at muscle-type receptors and an $E_{max}$ of 7% at ganglia-type receptors.

The foregoing is illustrative of the present invention and is not to be construed as limiting thereof. The invention is defined by the following claims, with equivalents of the claims to be included therein.

What is claimed is:

1. A compound having the formula:

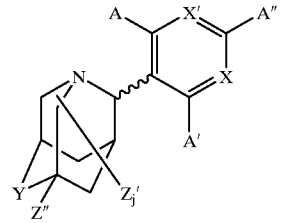

wherein X' is nitrogen and X is nitrogen or carbon bonded to a substituent selected from the group consisting of H, F, Cl, Br, I, R', NR'R", $CF_3$, OH, CN, $NO_2$, $C_2R'$, SH, $SCH_3$, $N_3$, $SO_2CH_3$, OR', SR', C(=O)NR'R", NR'C(=O)R', C(=O)R', C(=O)OR', $(CH_2)_qOR'$, OC(=O)R', OC(=O)NR'R", and NR'C(=O) OR', where R' and R" are individually hydrogen, $C_1$–$C_{10}$ alkyl, an aromatic group-containing species, and q is an integer from 1 to 6; A, A' and A" are the same substituents as the X substituents; Z' and Z" are substituents selected from the group consisting of alkyl, aryl, aralkyl, halo, hydroxyl, alkoxyl, alkylhydroxy, cyano, and mercapto; wherein Z" additionally can be hydrogen; j is an integer from 0 to 5; and the wavy line in the structure indicates that the compound can exist in the form of an enantiomer or a diasteromer; Y is C=O, C(OH)R' or CHA, where R' is hydrogen or lower alkyl.

2. The compound of claim 1, wherein A, A' and A" are hydrogen.

3. The compound of claim 1, wherein Z" is hydrogen.

4. The compound of claim 1, wherein j is 0.

5. The compound of claim 1, wherein A is selected from the group consisting of F, Cl, Br, I, R', NR'R", $CF_3$, OH, CN, $NO_2$, $C_2R'$, SH, $SCH_3$, $N_3$, $SO_2CH_3$, OR', SR', C(=O)NR'R", NR'C(=O)OR', C(=O)R', C(=O)OR', $(CH_2)_qOR'$, OC(=O)R', OC(=O)NR'R", and NR'C(=O) OR'.

* * * * *